(12) United States Patent
Kirton et al.

(10) Patent No.: US 11,224,713 B2
(45) Date of Patent: Jan. 18, 2022

(54) SUBSTANCE DELIVERY ARRANGEMENT FOR GAS THERAPY DEVICE

(71) Applicant: FISHER & PAYKEL HEALTHCARE LIMITED, Auckland (NZ)

(72) Inventors: Robert Stuart Kirton, Auckland (NZ); Kevin Peter O'Donnell, Auckland (NZ); Martin Paul Friedrich Kramer, Auckland (NZ); Stanislav Tatkov, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 656 days.

(21) Appl. No.: 15/528,740

(22) PCT Filed: Nov. 25, 2015

(86) PCT No.: PCT/NZ2015/050198
§ 371 (c)(1),
(2) Date: May 22, 2017

(87) PCT Pub. No.: WO2016/085354
PCT Pub. Date: Jun. 2, 2016

(65) Prior Publication Data
US 2017/0312472 A1 Nov. 2, 2017

Related U.S. Application Data

(60) Provisional application No. 62/084,359, filed on Nov. 25, 2014.

(51) Int. Cl.
*A61M 16/08* (2006.01)
*A61M 16/14* (2006.01)
(Continued)

(52) U.S. Cl.
CPC ....... *A61M 16/0833* (2014.02); *A61B 5/0813* (2013.01); *A61M 16/0069* (2014.02);
(Continued)

(58) Field of Classification Search
CPC ........... A61M 16/0057–0084; A61M 16/0833; A61M 16/1075–109; A61M 16/14;
(Continued)

(56) References Cited

U.S. PATENT DOCUMENTS 3,593,712 A * 7/1971 Weaver ............. A61M 15/0085
128/200.16
4,231,973 A 11/1980 Young et al.
(Continued)

FOREIGN PATENT DOCUMENTS

WO WO 2016/085354 6/2016

OTHER PUBLICATIONS

PCT Search Report and Written Opinion for PCT Application No. PCT/NZ2015/050198 dated Mar. 16, 2016 in 9 pages.
(Continued)

*Primary Examiner* — Margaret M Luarca
(74) *Attorney, Agent, or Firm* — Knobbe, Martens, Olson & Bear, LLP (57) ABSTRACT

A mount configured for use within a respiratory system that provides a structure that facilitates coupling of a nebuliser downstream of a humidifier chamber and upstream of a conduit that delivers conditioned breathing gases to a patient or user. The mount can couple together a chamber, a nebulizer and a conduit.

16 Claims, 9 Drawing Sheets

(51) Int. Cl.
*A61M 16/00* (2006.01)
*A61M 16/10* (2006.01)
*A61M 16/16* (2006.01)
*A61M 39/10* (2006.01)
*A61B 5/08* (2006.01)
*A61M 16/12* (2006.01)
*A61M 15/00* (2006.01)
*A61M 11/00* (2006.01)

(52) U.S. Cl.
CPC ...... *A61M 16/085* (2014.02); *A61M 16/0816* (2013.01); *A61M 16/0858* (2014.02); *A61M 16/109* (2014.02); *A61M 16/1095* (2014.02); *A61M 16/12* (2013.01); *A61M 16/14* (2013.01); *A61M 16/16* (2013.01); *A61M 16/161* (2014.02); *A61M 39/10* (2013.01); *A61M 39/105* (2013.01); *A61M 11/005* (2013.01); *A61M 15/0085* (2013.01); *A61M 2016/103* (2013.01); *A61M 2016/1025* (2013.01); *A61M 2205/3303* (2013.01); *A61M 2205/3331* (2013.01); *A61M 2205/3368* (2013.01); *A61M 2230/04* (2013.01); *A61M 2230/10* (2013.01); *A61M 2230/201* (2013.01); *A61M 2230/202* (2013.01); *A61M 2230/205* (2013.01)

(58) Field of Classification Search
CPC .. A61M 16/16–168; A61M 16/20–209; A61M 39/10; A61M 16/0816; A61M 16/085; A61M 16/0858; A61M 16/12; A61M 16/1095; F16L 31/02; F16L 41/021; F16L 47/26; F16L 47/28; F16L 47/32
USPC .......................................................... D13/155
See application file for complete search history.

(56) References Cited

U.S. PATENT DOCUMENTS

| | | | |
|---|---|---|---|
| 7,146,979 B2 * | 12/2006 | Seakins | A61M 16/08 128/203.17 |
| 2005/0229926 A1 | 10/2005 | Fink et al. | |
| 2012/0018910 A1 * | 1/2012 | Moreno | A61M 16/16 261/122.1 |
| 2012/0085343 A1 | 4/2012 | Cortez et al. | |
| 2013/0174840 A1 | 7/2013 | Gallem et al. | |
| 2014/0014103 A1 * | 1/2014 | Smaldone | A61M 16/14 128/203.12 |
| 2014/0137860 A1 * | 5/2014 | Lanier | A61M 16/0833 128/202.27 |
| 2014/0190482 A1 * | 7/2014 | Wade | A61M 15/0085 128/203.25 |
| 2015/0000652 A1 * | 1/2015 | Haveri | A61M 16/0833 128/202.27 |

OTHER PUBLICATIONS

International Preliminary Report on Patentability for PCT Application No. PCT/NZ2015/050198 dated Jun. 8, 2017 in 6 pages.

\* cited by examiner

SUBSTANCE DELIVERY ARRANGEMENT FOR GAS THERAPY DEVICE

INCORPORATION BY REFERENCE

Any and all applications for which a foreign or domestic priority claim is identified in the Application Data Sheet as filed with the present application are hereby incorporated by reference under 37 CFR 1.57. This application claims the priority benefit of U.S. Provisional Patent Application No. 62/084,359, filed Nov. 25, 2014, which is hereby incorporated by reference in its entirety.

In addition, WO2012/164407, filed 30 May 2012, which teaches several different smooth bore tubing configurations and which claims priority to U.S. Provisional Patent Application No. 61/492,970, filed 3 Jun. 2011, and U.S. Provisional Patent No. 61/610,109, filed 13 Mar. 2012, are hereby incorporated by reference in their entirety.

Moreover, PCT/NZ2013/000222, filed 4 Dec. 2013, which teaches several different smooth bore tubing configurations and which claims priority to U.S. Provisional Patent Application No. 61/733,360, filed 4 Dec. 2012, U.S. Provisional Patent Application No. 61/733,359, filed 4 Dec. 2012, U.S. Provisional Patent Application No. 61/877,622, filed 13 September 2013, U.S. Provisional Patent Application No. 61/877,566, filed 13 September 2013, U.S. Provisional Patent Application No. 61/877,784, filed 13 September 2013, and U.S. Provisional Patent Application No. 61/877,736, filed 13 September 2013, are hereby incorporated by reference in their entirety.

BACKGROUND

Technical Field

The present disclosure generally relates to respiratory therapy. More particularly, the present disclosure relates to nebuliser configurations for use with respiratory therapy systems.

Description of the Related Art

A patient dealing with respiratory illness, for example chronic obstructive pulmonary disease (COPD), can have difficulty engaging in effective respiration. This difficulty may be the result of a variety of physiological faults, including a breakdown of lung tissue, dysfunctions of the small airways, excessive accumulation of sputum, infection, genetic disorders, or cardiac insufficiency. With such illnesses, it is useful to provide the patient with a therapy that can improve the ventilation of the patient. In some situations, the patient can be provided with a respiratory therapy system that includes a gas source, an interface that may be used to transmit gas to an airway of a patient, and a conduit extending between the gas source and the interface. Gas delivered to an airway of the patient from the gas source can help to promote adequate ventilation of the patient. The gas source may, for example, be a container of air and/or another gas suitable for inspiration, e.g., oxygen or nitric oxide, a mechanical blower capable of propelling a gas through the conduit to the interface, or some combination of the above. The respiratory therapy system can include a gas humidifier that can humidify and heat gases passing through the respiratory therapy system to improve patient comfort and/or improve the prognosis of the patient's respiratory illness. The gas humidifier can include a water reservoir and a heating element for heating the water in the reservoir. As the water heats up, water vapor is formed, which can join the stream of gases passing through the gas humidifier.

It can be advantageous to use a nebuliser with a respiratory therapy system to, for example, deliver a medicinal substance to an airway of a patient along with the delivery of respiratory gases to the airway of the patient. In some cases, the nebuliser can be actuated such that the nebulised substance is propelled along the conduit extending between the gas source and the patient interface. The flow passing along the conduit from the gas source to the patient interface can aid in guiding the substance to the patient's airway. However, the efficiency of substance delivery may be lower than desired. A considerable portion of a dose of the medicinal substance may, for example, stick to, settle along or become caught on an internal wall of the conduit and not progress to the patient's airway, particularly if moisture (e.g., introduced by a humidifier used with the respiratory therapy system) has been deposited on the internal wall of the conduit. The diminished amount of the substance delivered to the patient can reduce the efficacy of the therapy.

SUMMARY

Certain features, aspects and advantages of at least one of the configurations disclosed herein include the realization that heated smooth bore tubing may be used to convey both respiratory gases and nebulised substances to a patient's airway. The smooth bore of the tubing may improve the efficiency of substance transportation by reducing the tendency of the substance to stick to or be caught on the internal walls of the tubing. Additionally, particularly when a gas humidifier is used, the heat applied to the tubing may reduce the condensation of moisture along the internal walls of the tubing, which also reduces the tendency of the substance to not travel the length of the tubing to the interface. When the tube is dry, the tube is hydrophobic, but when the tube becomes wet due to condensation, the tube loses its hydrophobicity making the tube more likely to retain droplets of substance on the wall of the tube.

According to an aspect of the present disclosure, there is provided a mount configured for use within a respiratory system, the mount being configured to join together a chamber, a flow-generating respiratory apparatus, and a third component, the mount comprising a duct, the duct defining a three-way port, the duct configured to connect to an outflow port of the chamber, and the duct comprising an auxiliary port for interaction with a flow through the duct.

The auxiliary port may be configured for connection to at least one of a nebuliser, a sensor, and a source of a trace gas.

The duct may comprise a bend.

The mount may further comprise a second duct, the second duct may have a bend and be configured to connect to an inflow port of the chamber.

The auxiliary may port receive a cap, the cap may form a removable sealed closure for the port.

The auxiliary port may be sized and configured to receive a nebuliser. The auxiliary port may be sized and configured to receive at least one of a sensor, and a source of a trace gas.

According to another aspect of the present disclosure, there is provided a respiratory therapy system comprising: a flow generator adapted to deliver gases to a patient; a patient interface; a gas passageway extending between the flow generator and the patient interface; and a nebuliser adapted to deliver a substance to at least a first portion of the gas passageway, wherein at least a section of the gas passageway at and/or downstream of the first portion comprises a smooth bore conduit.

A gas humidifier may be present at a point along the gas passageway.

The first portion may be downstream of the gas humidifier.

The smooth bore conduit may comprise a conduit heater.

The conduit heater may be located substantially outside of the flow path of gases passing through the smooth bore conduit.

According to another aspect of the present disclosure, there is provided a mount configured to couple a chamber to a flow-generating respiratory apparatus, the mount comprising a duct configured to connect to one of an inlet port or an outlet port of the chamber, the duct also comprising an auxiliary port such that the duct comprises a 3-way port, the duct having a flow inlet end and a flow outlet end with the auxiliary port being positioned between the inlet end and the outlet end.

The duct may be configured to connect to the outlet port of the chamber.

The duct may comprise a bend.

The mount may also comprise a second duct configured to connect to the inlet port of the chamber.

The auxiliary port may receive a cap, the cap may form a removable sealed closure for the port.

The auxiliary port may be sized and configured to receive at least one of a nebulizer, a sensor, and a source of a trace gas.

According to another aspect of the present disclosure, there is provided a
- a nebuliser mount configured to couple a chamber to a respiratory apparatus, the nebuliser mount comprising an outflow duct, the outflow duct being configured to connect a post-chamber port of the respiratory apparatus, a chamber outlet port and a nebuliser port.

The nebuliser mount may comprise a cap that is connected to the mount and that is configured to close the nebuliser port.

The nebuliser mount may further comprise an inflow duct, the inflow duct may be configured to connect a pre-chamber port of the respiratory apparatus and a chamber inlet port.

A first end of the inflow duct may be separated from a first end of the outflow duct by a first distance between flow passage centers and a second end of the inflow duct may be separated from a second end of the outflow duct by a second distance between flow passage centers that is greater than the first distance.

The outflow duct and the inflow duct may be integrated into a single structure.

A bridge may join the outflow duct and the inflow duct.

The nebuliser mount may further comprise an outflow collar that defines at least a portion of a fitting configured to join the outflow duct to the post-chamber port and a medical taper may be formed on an inner surface of the outflow collar.

The outflow collar may comprise a first axis and a portion that is configured to connect to the chamber outlet port may comprise a second axis, the first axis and the second axis being generally normal to each other.

The outflow duct may comprise a first portion and a second portion, the first portion being connected to the second portion by an elbow.

The nebuliser port may be aligned with the first portion.

The nebuliser port may be aligned with the second portion.

The first portion may extend vertically.

The second portion may extend horizontally.

The second portion may comprise a first collar, the first collar being positioned adjacent to the part of the mount that may be configured to connect to the post-chamber port, and wherein the nebuliser port may be surrounded by a second collar.

The first collar and the second collar may be disposed at opposite ends of the second portion of the outflow duct.

BRIEF DESCRIPTION OF THE DRAWINGS

Specific embodiments and modifications thereof will become apparent to those skilled in the art from the detailed description having reference to the figures that follow, of which.

DETAILED DESCRIPTION

Overall System

Figure 1:
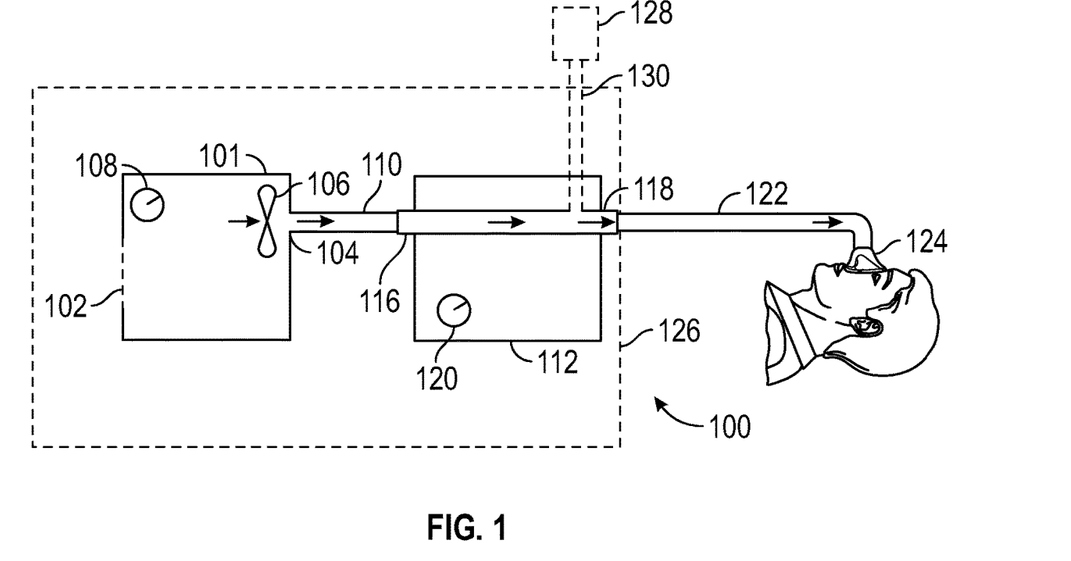
FIG. 1 shows a schematic diagram of a respiratory therapy system.

With reference to FIG. 1, a configuration for a respiratory therapy system 100 is shown. In the illustrated configuration, the respiratory therapy system 100 may comprise a flow generator 101.

The illustrated flow generator 101 comprises a gas inlet 102 and a gas outlet 104. The flow generator 101 also may comprise a blower 106. The blower 106 can draw in gas from the gas inlet 102. In some configurations, the flow generator 101 can comprise a source or container of compressed gas (e.g., air, oxygen, etc.). The container can comprise a valve that can be adjusted to control the flow of gas leaving the container. In some configurations, the flow generator 101 can use such a source of compressed gas and/or another gas source in lieu of the blower 106. In some configurations, the blower 106 can be used in conjunction with another gas source. In some configurations, the blower 106 can comprise a motorized blower or can comprise a bellows arrangement or some other structure capable of generating a gas flow. In some configurations, the flow generator 101 draws in atmospheric gases through the gas inlet 102. In some configurations, the flow generator 101 is adapted both to draw in atmospheric gases through the gas inlet 102 and to accept other gases (e.g., oxygen, nitric oxide, carbon dioxide, etc.) through the same gas inlet 102 or a different gas inlet. Other configurations also are possible.

The illustrated flow generator 101 comprises a user control interface 108. The user control interface 108 can comprise one or more buttons, knobs, dials, switches, levers, touch screens, speakers, displays, and/or other input or output modules that a user might use to input commands into the flow generator 101, to view data, and/or to control operations of the flow generator 101, and/or to control operations of other aspects of the respiratory therapy system 100.

The flow generator 101 can direct gas through the gas outlet 104 to a first conduit 110. In the illustrated configuration, the first conduit 110 channels the gas to a gas humidifier 112.

The gas humidifier 112 is used to entrain moisture in the gas in order to provide a humidified gas stream. The illustrated gas humidifier 112 comprises a humidifier inlet 116 and a humidifier outlet 118. The gas humidifier 112 can comprise, be configured to contain or contain water or another humidifying or moisturizing agent (hereinafter referred to as water).

In some configurations, the gas humidifier 112 comprises a heating element (not shown). The heating element can be used to heat the water in the gas humidifier 112 to encourage water vaporization and/or entrainment in the gas flow and/or increase the temperature of gases passing through the gas humidifier 112. The heating element can, for example, comprise a resistive metallic heating plate. However, other heating elements are contemplated. For example, the heating element could comprise a plastic electrically conductive heating plate or a chemical heating system having a controllable heat output.

In the illustrated configuration, the gas humidifier 112 comprises a user control interface 120. The user control interface 120 comprises one or more buttons, knobs, dials, switches, levers, touch screens, speakers, displays and/or other input or output modules that a user might use to input commands into the gas humidifier 112, to view data, and/or to control operations of the gas humidifier 112, and/or control operations of other aspects of the respiratory therapy system 100.

In some configurations, the flow generator 101 and the gas humidifier 112 may share a housing 126. In some configurations, the gas humidifier 112 may share only part of the housing 126 with the flow generator 101. Other configurations also are possible.

In the illustrated configuration, gas travels from the humidifier outlet 118 to a second conduit 122. The second conduit 122 can comprise a conduit heater (e.g., see wires 308 in FIG. 16). The conduit heater can be used to add heat to gases passing through the second conduit 122. The heat can reduce or eliminate the likelihood of condensation of water entrained in the gas stream along a wall of the second conduit 122. The conduit heater can comprise one or more resistive wires located in, on, around or near a wall of the second conduit 122. In one or more configuration, such one or more resistive wires can be located outside of any gas passage. In one or more configurations, such one or more resistive wires are not in direct contact with the gases passing through the second conduit 122. In one or more configurations, a wall or surface of the second conduit 122 intercedes between the one or more resistive wires and the gases passing through the second conduit 122.

Gas passing through the second conduit 122 can be delivered to a patient treatment interface 124. The patient treatment interface 124 can pneumatically link the respiratory therapy system 100 to an airway of a patient. In some configurations, the respiratory therapy system 100 utilizes a two-limb system comprising separate inspiratory and expiratory gas passageways that interface with one or more airways of the patient.

The patient treatment interface 124 can comprise a sealing or non-sealing interface, and can comprise a nasal mask, an oral mask, an oro-nasal mask, a full face mask, a nasal pillows mask, a nasal cannula, an endotracheal tube, a combination of the above or some other gas conveying system. In some configurations, a short length of tubing connects the interface to the second conduit 122. In some configurations, the short length of tubing can have a smooth bore, as described elsewhere herein. For example, a short flexible length of tubing can connect a nasal cannula or the like to the second conduit 122. The short length of tubing connecting the interface to the second conduit 122 may be breathable such that it allows the transmission of vapour through the wall of the tube. In some configurations, the short length of tubing can incorporate one or more heating wires as described elsewhere herein. The smooth bore, whether heated or not, can improve the efficiency in delivering nebulised substances, as described elsewhere herein. Any other suitable patient treatment interface 124 can be used.

With continued reference to FIG. 1, in some configurations, a nebuliser 128 can be used with the respiratory therapy system 100. In some configurations, if a nebuliser 128 is used, the flow generator 101, the gas humidifier 112, and the nebuliser 128 can share the housing 126. In some configurations, the nebuliser 128 is separate of the housing 126. The nebuliser 128 can be linked to a portion of the gas passageway extending between the flow generator 101 (which may include the gas inlet 102) and the patient interface 124, although other arrangements for the nebuliser 128 or another nebuliser may be utilized. In some configurations, the nebuliser 128 is not positioned in-line in any location between the humidifier outlet 118 and the patient interface 124. Rather, the nebuliser 128 is positioned upstream of the humidifier outlet 118 or upstream of the inlet to the second conduit 122. In some configurations, the nebuliser 128 can be positioned upstream of an inlet into the humidifier. In some configurations, the nebulizer 128 can be positioned between the source of gases flow and the chamber.

The nebuliser 128 can comprise a substance (e.g., a medicinal substance, trace gases, etc.) that can be introduced into the gas flow. The substance can be caught up in the gas flow and can be delivered along with respiratory gases to an airway of the patient. The nebuliser 128 can be linked to the portion of the gas passageway by a conveyor 130, which can comprise a conduit or an adaptor. Alternatively, the nebuliser 128 can interface directly with the gas passageway, which can render the conveyor 130 unnecessary. For convenience, the term "nebuliser" has been used to identify a component or assembly capable of introducing any desired substance into the gases flow. In some configurations, a sensor, probe or the like can also be introduced into the gases flow. As used herein, the term "introduced element" encompasses both substances (e.g., medicines, medicaments, trace gases, and the like) as well as components (e.g., sensors, probes, and the like).

In the illustrated configuration, and as implied above, the respiratory therapy system 100 can operate as follows. Gas can be drawn into the flow generator 101 through the gas inlet 102 due to the rotation of an impeller of the motor of the blower 106. The gas is propelled out of the gas outlet 104 and through the first conduit 110. The gas enters the gas humidifier 112 through the humidifier inlet 116. Once in the gas humidifier 112, the gas entrains moisture when passing over or near water in the gas humidifier 112. The water is heated by the heating element, which aids in the humidification and/or heating of the gas passing through the gas humidifier 112. The gas leaves the gas humidifier 112 through the humidifier outlet 118 and enters the second conduit 122. Prior to entering the second conduit 122, the gas receives one or more substance from the nebuliser. The gas is passed from the second conduit 122 to the patient interface 124, where the gas is taken into the patient's airways to aid in the treatment of respiratory disorders.

Respiratory Therapy System With First Adaptor Configuration

Figure 2:
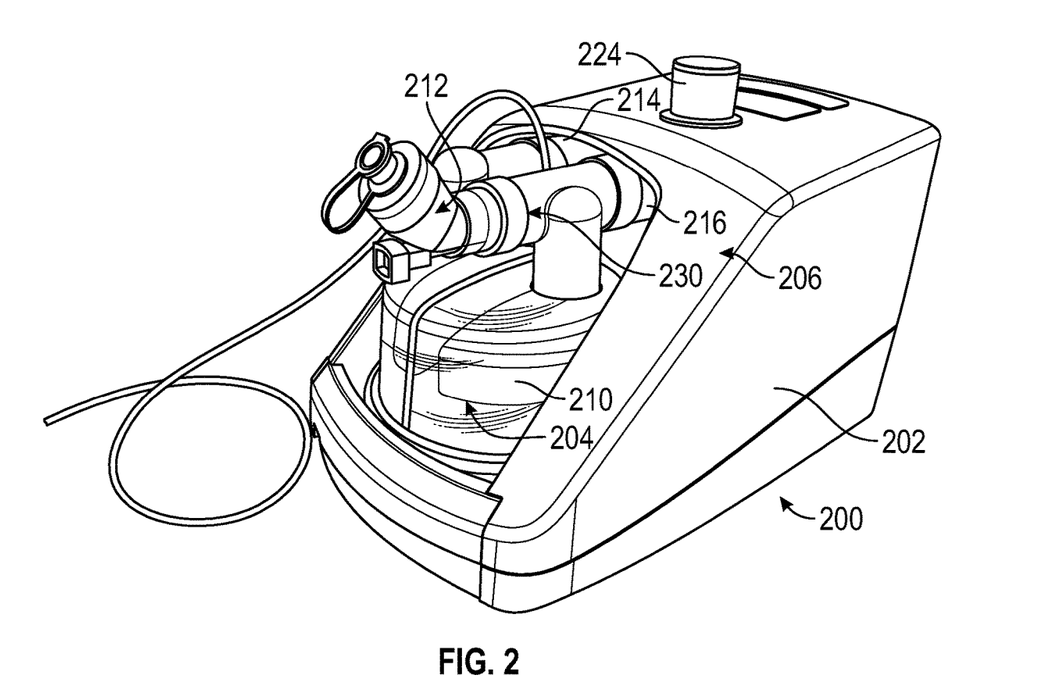
FIG. 2 is a perspective of a respiratory therapy system arranged and configured in accordance with certain features, aspects and advantages of the present embodiment.

FIG. 2 illustrates an embodiment of a respiratory therapy system 200 similar to that described in FIG. 1.

In the configuration illustrated in FIG. 2, the respiratory therapy system 200 incorporates a humidifier with an integrated flow generator. In other words, in the illustrated configuration, a housing 202 contains a flow generator (not shown) and at least a portion of a gas humidifier 204. In the illustrated configuration, the flow generator and the gas humidifier 204 together form an integrated unit 206. In some configurations, the humidifier with the integrated flow generator can be the apparatus sold under the name AIRVO™ 2 by Fisher & Paykel Healthcare. Such an apparatus is shown and described, for example, in U.S. Pat. No. 7,111,624, which is hereby incorporated by reference in its entirety. Any other suitable configuration can be used and the configuration of FIG. 2 can be configured with any of the components or configurations described above. Specifically, the flow generator and the humidifier need not be an integrated unit; however, solely for simplicity of description, the following discussion will simply refer to the integrated unit 206.

The gas humidifier 204 in the illustrated integrated unit 206 employs a chamber 210. The chamber 210 can have any suitable configuration, including any configuration shown and/or described in U.S. Pat. No. 7,146,979 and/or U.S. Pat. No. 6,349,722, each of which is hereby incorporated by reference in its entirety. The chamber 210 can contain or hold a volume of liquid, such as water, that is used to humidify gases as they pass through the chamber. In some configurations, the chamber 210 simply defines a location in the system where liquid, such as water, is transferred into the gases stream or flow of gases.

As discussed above, gases that have been conditioned (e.g., heated and/or humidified) within the integrated unit 206 can be conveyed to a patient or other user. In some configurations, a tube or conduit (not shown) is used to convey the gases to the patient or other user. Some examples of conduits or tubes that can be used with the integrated unit 206 include, but are not limited to, those shown and described in U.S. Patent Publication No. 2014/0202462A1 (also published as WO2012/164407A1) and WO2014/088430, each of which being hereby incorporated by reference in its entirety. Any other suitable conduits or tubes also can be used.

With continued reference to FIG. 2, a nebuliser 212 can be attached to the integrated unit 206. In some configurations, the nebuliser 212 can be positioned upstream of the humidifier chamber 210. In some configurations, the nebuliser 212 can be positioned downstream of the humidifier chamber 210. In some configurations, a cap (shown in FIG. 4) can close the location at which the nebuliser 212 can attach when the nebuliser is not attached to the integrated unit 206. The cap can have any suitable configuration. In some configurations, the cap overlies the nebuliser port. In some configurations, the cap inserts into the nebuliser port. The cap can be tethered to the mount 230. By connecting the cap at or proximate to the nebuliser port, the cap is less likely to be misplaced when the nebuliser 212 is inserted into the nebuliser port (and the cap is removed). In some configurations, the cap is a silicone component. In some configurations, the cap incorporates one or more sealing elements. In some configurations, the cap incorporates one or more silicone sealing elements.

The nebuliser 212 produces a fine spray of liquid. The fine spray of liquid is introduced into the flow of conditioned gases or pre-conditioned gases. Any suitable nebuliser 212 can be used. In some configurations, the nebuliser 212 is the Aerogen Aeroneb® Solo nebuliser. In the illustrated configuration, an outlet of the nebuliser 212 is positioned between the chamber 210 and the conduit or tube 122. In some configurations, the nebuliser 212 is configured and positioned to inject the fine spray of liquid into a conditioned gas flow downstream of the chamber 210 and upstream of the conduit 122 that connects a patient interface to the integrated unit 206. In some configurations, the nebuliser 212 is configured and positioned to inject the fine spray of liquid into the conditioned gas flow downstream of the chamber 210 and upstream of a connection location of the removable conduit 122 and the integrated unit 206. In some configurations, the nebuliser 212 is configured and positioned to inject the fine spray of liquid into the gas flow prior to entry into the chamber 210. In some configurations, the nebuliser 212 is configured and positioned to inject the fine spray of liquid into the gas flow during entry into the chamber 210. In some configurations, the nebuliser 212 is configured and positioned to inject the fine spray of liquid into the gas flow following entry into the chamber 210. In some configurations, the nebuliser 212 is configured and positioned to inject the fine spray of liquid into the gas flow prior to exit from the chamber 210. In some configurations, the nebuliser 212 is configured and positioned to inject the fine spray of liquid into the gas flow during exit from the chamber 210. In some configurations, the nebuliser 212 is configured and positioned to inject the fine spray of liquid into the gas flow following exit from the chamber 210. In some of these configurations, rather than injecting a fine spray of liquid or having the nebuliser, other substances can be injected in the identified locations or other components, such as a sensor or the like, can be inserted in the identified locations.

Figure 3:
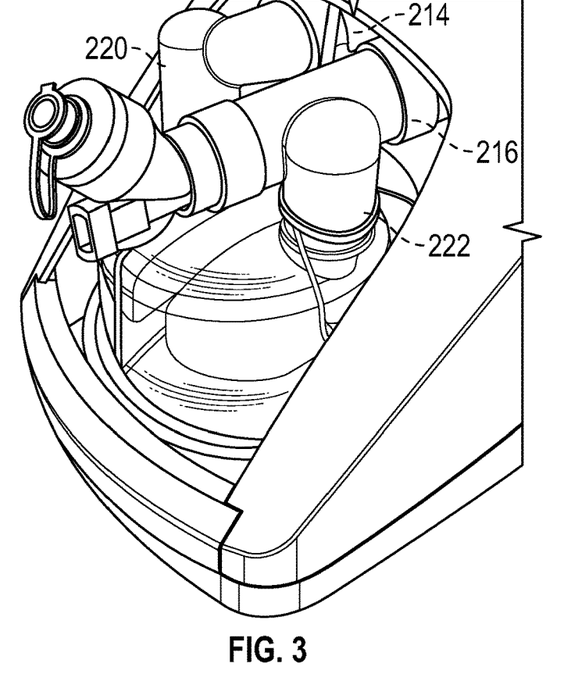
FIG. 3 is an enlarged view of a portion of the system of FIG. 2.

In the illustrated configuration, the integrated unit 206 comprises a pre-chamber port 214 and a post-chamber port 216. As shown in FIG. 3, the pre-chamber port 214 receives flow from the flow generator and delivers the flow into the chamber 210 through a chamber inlet port 220. Flow is delivered from a chamber outlet port 222 to the post-chamber port 216. With reference again to FIG. 2, the post-chamber port 216 is fluidly connected to a unit outlet port 224. In some configurations, the post-chamber port 216 and the unit outlet port 224 are opposing ends of a single conduit or lumen. Other configurations are possible. The unit outlet port 224 can connect with the hose or conduit 122 such that gases can be conveyed from the integrated unit 226 to the patient interface 124. The hose or conduit can be removably attached to the unit outlet port 224.

Figure 9:
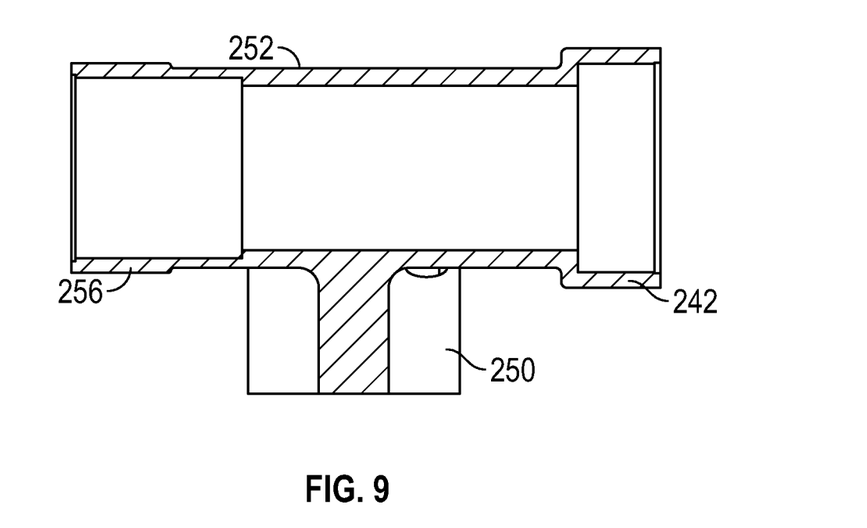
Figure 10:
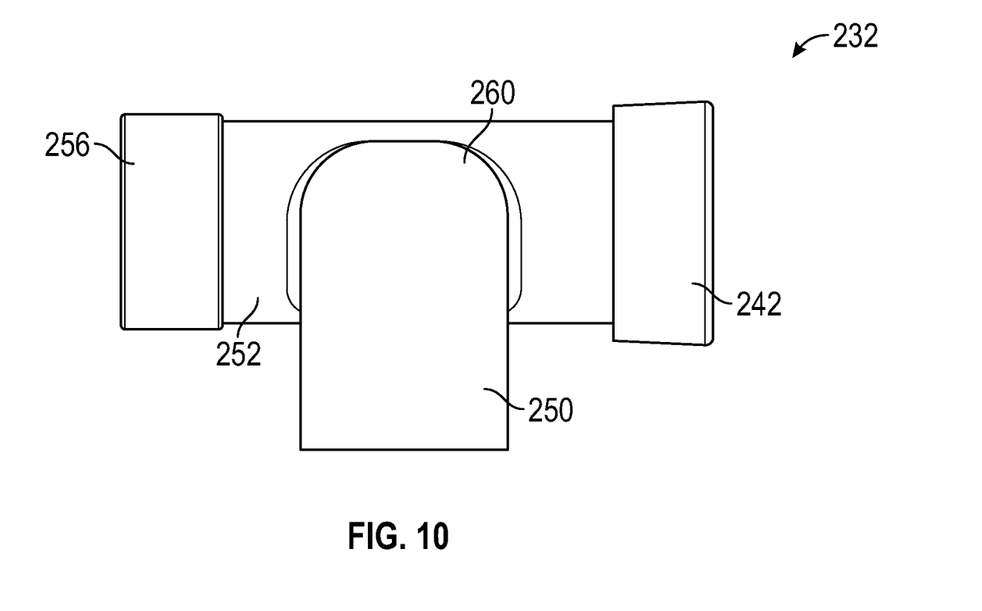

With reference to FIG. 2, a mount 230 is used to join together the chamber 210, the integrated unit 206 and the nebuliser 212 or other suitable component. As will be described, the mount 230 facilitates the introduction of the fine mist from the nebuliser 212 into gases traveling from the chamber 210 to the unit outlet port 224, which gases ultimately travel to the conduit or tube that delivers the gases from the integrated unit 206 to the patient interface. Where other components are used, the mount can facilitate the introduction of other substances (e.g., a medicament, a trace gas, nitric oxide or the like) or components (e.g., a sensor, or the like).

With reference now to FIG. 4, the illustrated mount 230 is arranged and configured to connect at least the chamber outlet port 222 and the post-chamber port 216 while also connecting to the nebuliser 212 with a nebuliser port 234. In some configurations, the mount 230 is arranged and configured to connect at least the chamber inlet port 220 and the pre-chamber port 214 while also connecting to the nebuliser with the nebuliser port 234. In some configurations, the nebuliser 212 is supported by the nebuliser port 234. An outflow duct 232 connects at least the chamber outlet port 222 and the post-chamber port 216. In the illustrated configuration, the outflow duct 232 also connects the nebuliser port 234 and the post-chamber port 216. Thus, in the illustrated configuration, the outflow duct 232 connects the post-chamber port 216 of the integrated unit 206, the chamber outlet port 222 of the chamber 210 and the nebuliser port 234. Broadly speaking, the mount 230 is adapted to connect the nebulizer 212, the chamber 210 and the integrated unit 206.

In the illustrated configuration, the mount 230 also is arranged and configured to connect the chamber inlet port 220 and the pre-chamber port 214. In particular, an inflow duct 236 connects the pre-chamber port 214 and the chamber inlet port 220. Other configurations are possible.

In the illustrated configuration, as shown in FIGS. 6-13, the mount 230 can comprise the outflow duct 232 and the inflow duct 236 in a single structure. While providing the outflow duct 232 and the inflow duct 236 as separate components is possible, integrating or physically connecting the two ducts 232, 236 simplifies assembly and reduces the likelihood of misplacing one of the two ducts 232, 236. In addition, integrating or physically connecting the two ducts 232, 236 provides visual guidance regarding proper installation orientation. In the illustrated configuration, a bridge 240 spans a distance between a portion of the outflow duct 232 and a portion of the inflow duct 236. The bridge 240 joins the two ducts 232, 236.

In the illustrated configuration, a collar 242 defines at least a portion of a fitting that is used to join the outflow duct 232 to the post-chamber port 216. Similarly, another collar 244 defines at least a portion of a fitting that is used to join the inflow duct 236 to the pre-chamber port. Each of the collars 242, 244 can include a medical taper on an inner surface. The medical tapers can be used to couple and seal the ducts 232, 236 to the ports 214, 216 of the integrated unit 206. Other securing arrangements (e.g., tapers, threads, friction fits, luer locks, interlocking mechanical components, etc.) also can be used.

In the illustrated configuration, the bridge 240 joins the collars 242, 244 of the ducts 232, 236. By positioning the bridge 240 on the collars 242, 244, the bridge 240 can be positioned in a region of the integrated unit 206 that will be out of the way of other components of the system 200. As shown in FIG. 13, the illustrated bridge 240 can have an inverted U-shape with a hollow center, for example but without limitation.

In the illustrated configuration, the bridge 240 also includes a mount 246. The mount 246 can comprise two fingers, ears, tabs or the like. The mount 246 is sized and configured to receive a tube of a feedset. The feedset is a component that can attach to a liquid source, such as an IV bag, and that can define a passage for fluid to flow into the chamber. The illustrated mount 246 faces outward or away from the ports 214, 216 of the integrated unit 206. Such a positioning allows securing of the feedset with the mount 246 while the chamber 210 is docked into the integrated unit 206.

With continued reference to FIGS. 6-13, the mount 230 is arranged and configured to connect the ports 214, 216 of the integrated unit 206 with the ports 220, 222 of the chamber 210. The ports 214, 216 extend horizontally while the ports 220, 222 extend vertically. In some configurations, the portion of the mount 230 that is arranged and configured to connect to the ports 214, 216 of the integrated unit comprise first axes and the portion of the mount 230 that is arranged and configured to connect to the ports 220, 222 of the chamber comprise second axes that are generally normal to the first axes. In addition, in the illustrated configuration, the ports 214, 216 have a smaller centerline distance relative to the ports 220, 222. In other words, a first end of the inflow duct is separated from a first end of the outflow duct by a first distance between flow passage centers and a second end of the inflow duct is separated from a second end of the outflow duct by a second distance between flow passage centers that is greater than the first distance. Thus, the mount 230 is arranged and configured to alter the direction of flow from one end of the ducts 232, 236 to the other end of the ducts 232, 236 while also adjusting the centerline distance, or gap between the ducts, from one end of the ducts 232, 236 to the other end of the ducts 232, 236.

As illustrated in FIG. 6, the outflow duct 232 comprises a first portion 250 and a second portion 252 that are connected at a bend or elbow 254. In the illustrated configuration, the first portion 250 extends vertically. In the illustrated configuration, the second portion 252 extends horizontally. Other configurations are possible. The first portion 250 can include an internal taper or the like. The first portion seals or mates with an outer surface of the chamber outlet port 222. The second portion can include the collar 242. As described above, the collar 242 seals or mates with the post-chamber port 216.

In the illustrated configuration, the second portion 252 comprises a second collar 256. The second collar 256 can be at an opposite end of the second portion 252 relative to the collar 242. In the illustrated configuration, the bend 254 is interposed between the two collars 242, 256. The second collar 256 can be sized and configured to mate or seal with the nebuliser 212. The second collar 256 defines a port. In some configurations, the port can be an auxiliary port that is configured to receive one or more auxiliary components. For example, the auxiliary components can include a nebuliser 212. In the illustrated configuration, the nebuliser 212 is received within the second collar 256. More particularly, in the illustrated configuration, the inner surface of the second collar 256 includes a tapered surface that mates or seals with the outer surface of the nebuliser 212. Other configurations are possible.

As illustrated in FIG. 8, the first collar 242 and the second collar 256 are disposed at opposite ends of the second portion 252 of the outflow duct 232. The second portion 252 of the illustrated outflow duct 232 is a straight section of tubing or the like. In other words, in the illustrated configuration, the first collar 242 and the second collar 256 are aligned along a single axis that extends through the second portion 252 of the outflow duct 232. In some configurations, a single plane that extends along the central axis of the second portion 252 of the outflow duct 232 bisects the first collar 242 and the second collar 256, as shown in FIG. 9. As also shown in FIG. 9, while there is a lumen defined within the first portion 250 of the outflow duct 232, if the single plane extends vertically and along the central axis of the second portion 252 of the outflow duct 232, the single plane does not intersect the lumen defined within the first portion 250. Rather, such a plane intersects a wall that defines the lumen of the first portion 250. Other configurations are possible.

Figure 11:
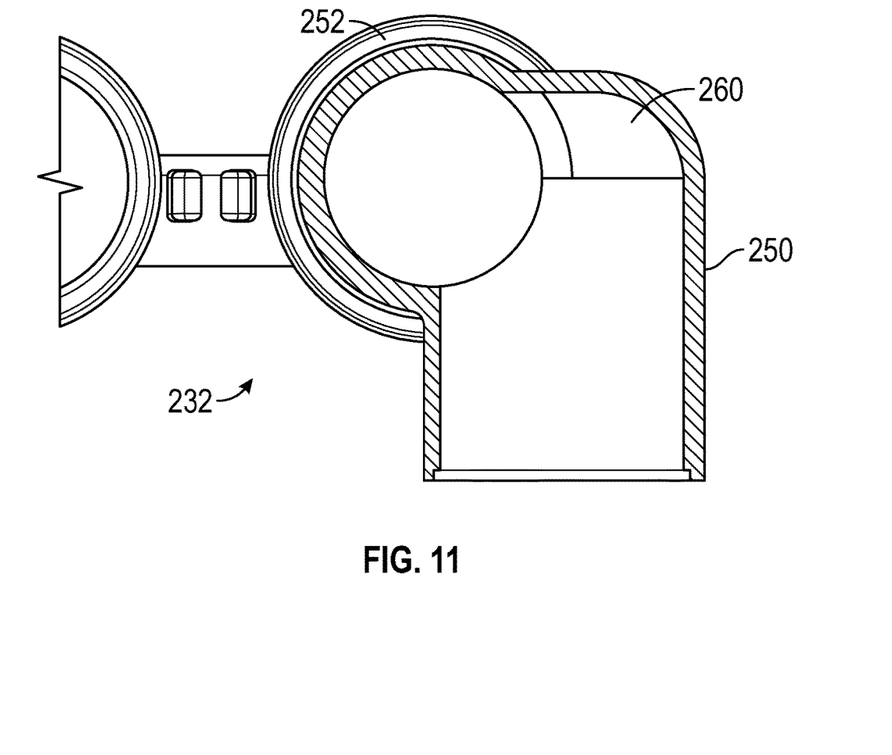
Figure 12:
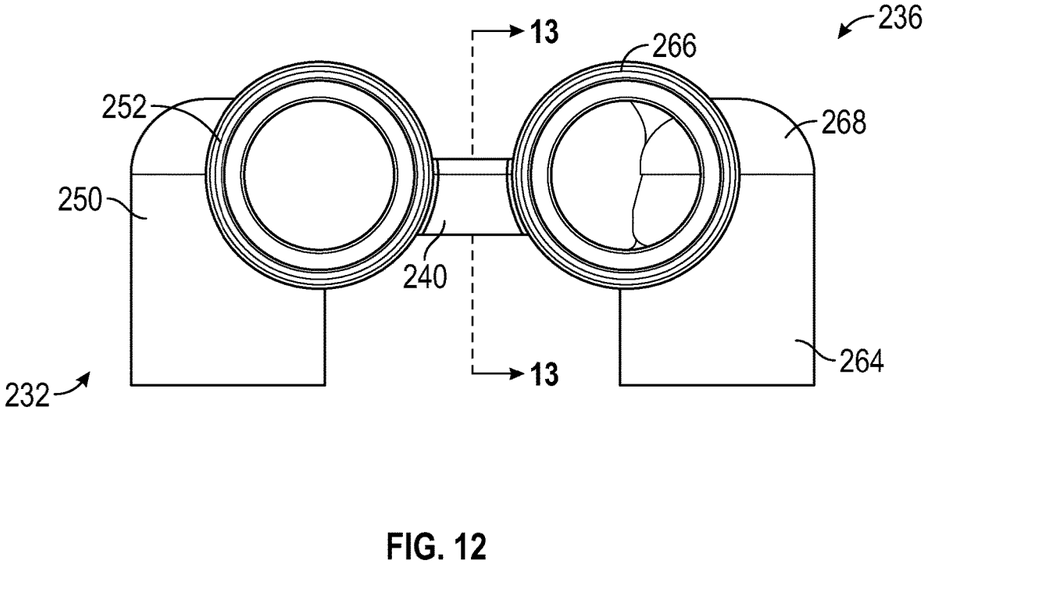
Figure 13:
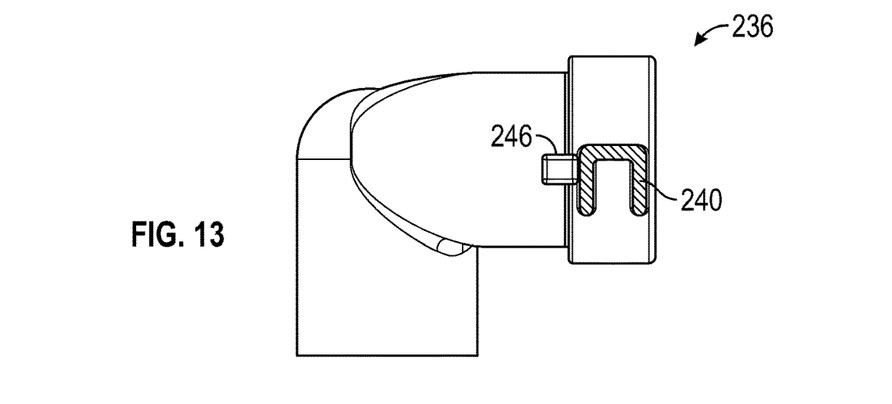

With reference to FIG. 11, as shown, a curved wall 260 is positioned at or adjacent to an intersection of the first portion 250 and the second portion 252 of the outflow duct 232. The curved wall 260 induces a flow at the transition between the first portion 250 and the second portion 252 to aid maintaining the fine mist from the nebuliser 212 in suspension within the conditioned gas flow. Other configurations are possible.

Figure 7:
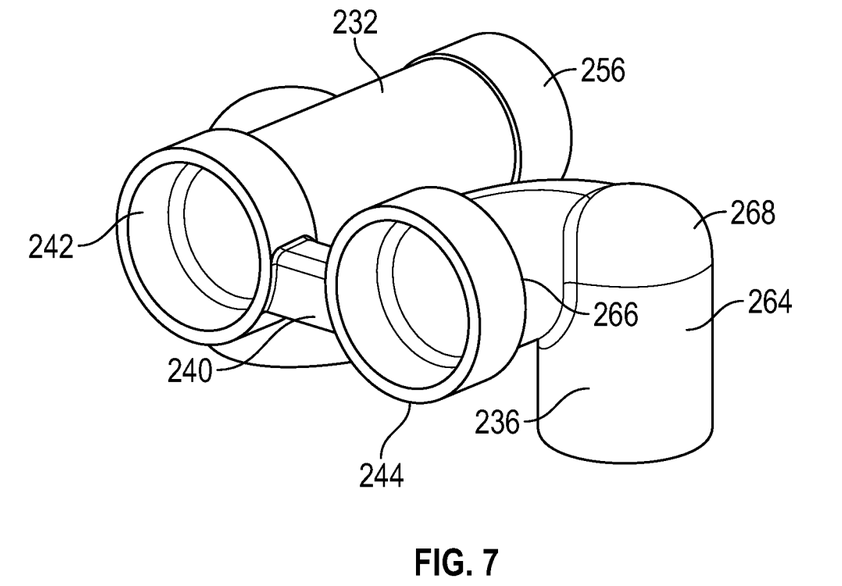
Figure 8:
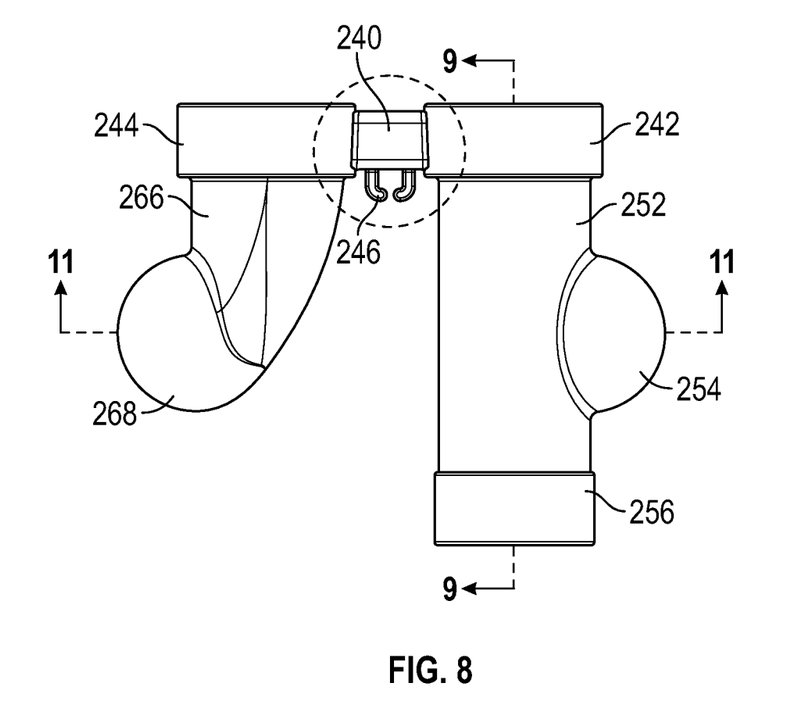

With reference to FIG. 7, the inflow duct 236 comprises a first portion 264 and a second portion 266 Like the outflow duct 232, the first portions 264 and the second portion 266 are not axially aligned. The first portion 264 is vertical. The second portion 266 is horizontal. The two portions 264, 266 are joined at a bend or elbow 268. The first portion 264 mates or seals with the chamber inlet port 220. The collar 242 of the second portion 266 mates or seals with the pre-chamber port 216.

Figure 4:
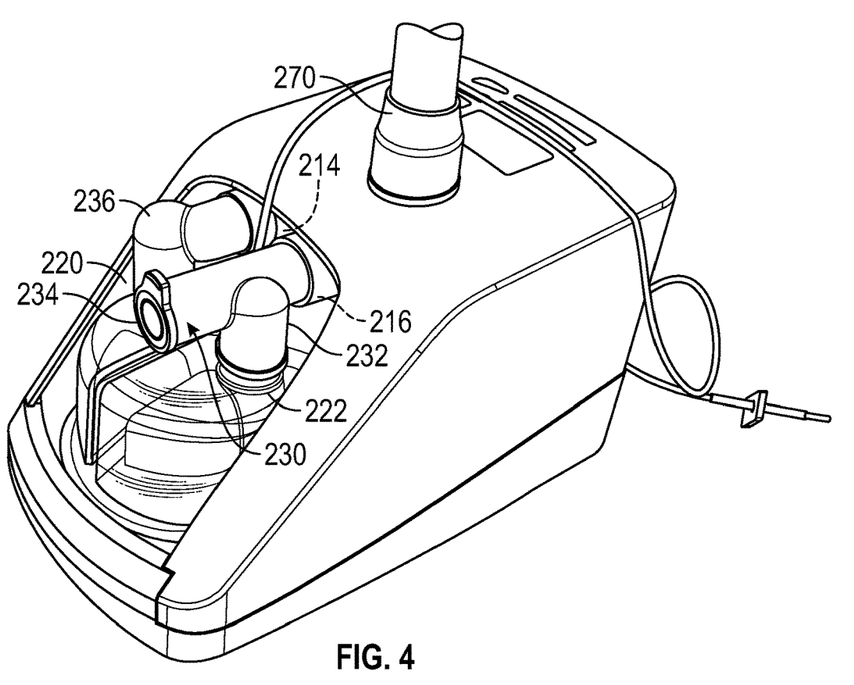
FIG. 4 is a perspective view of the system of FIG. 2 with the nebuliser removed and a cap in place.
Figure 5:
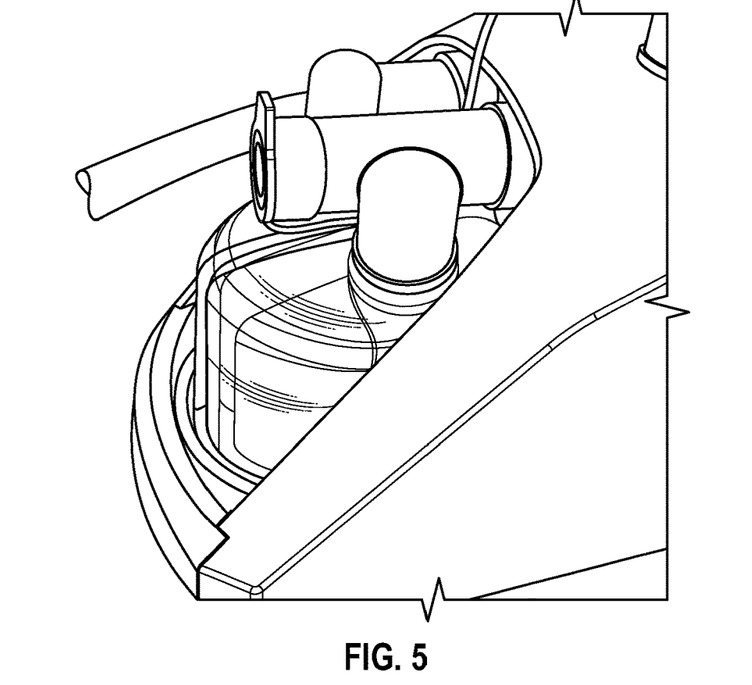
FIG. 5 is an enlarged view of a portion of the system of FIG. 4.
Figure 6:
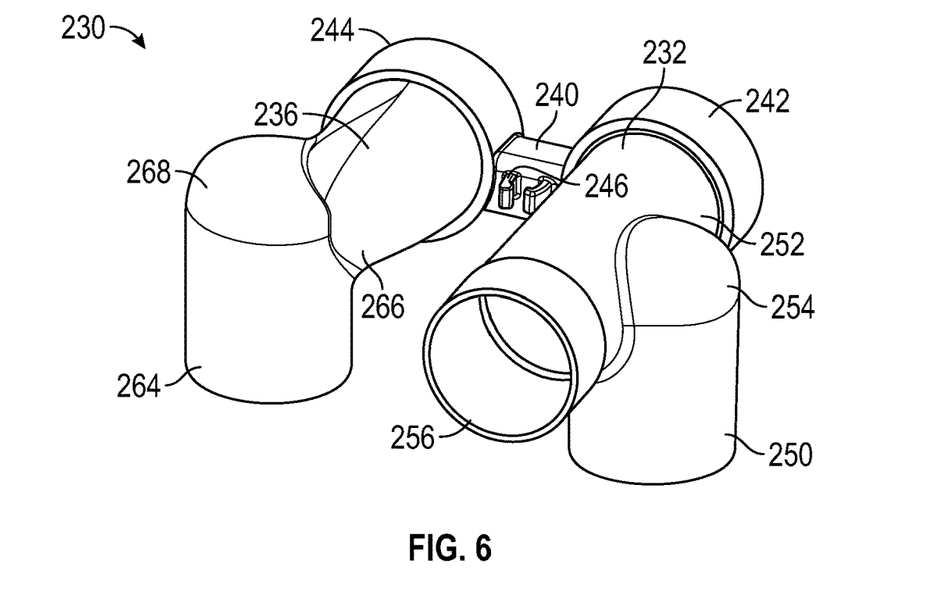
FIGS. 6-13 are views of a mount that is arranged and configured in accordance with certain features, aspects and advantages of the present embodiment, which mount is shown in FIGS. 2-5.

With the mount 230 in position, gases pass from the flow generator to the pre-chamber port 220. From the pre-chamber port 220, the gases pass through the inflow duct 236 to the chamber inlet port 220. From the chamber inlet port 220, the gases flow through the chamber 210 and gain heat and/or humidity before flowing out of the chamber outlet port 222. From the chamber outlet port 222, the gases pass through the outflow duct 232 before flowing to the post-chamber port 216. From the post-chamber port 216, the gases flow to the unit outlet port 224. As shown in FIG. 4, a conduit 270 can be connected to the unit outlet port 224 and the gases can travel through the conduit 270 to the patient or other user.

Respiratory Therapy System With Second Adaptor Configuration

Figure 14:
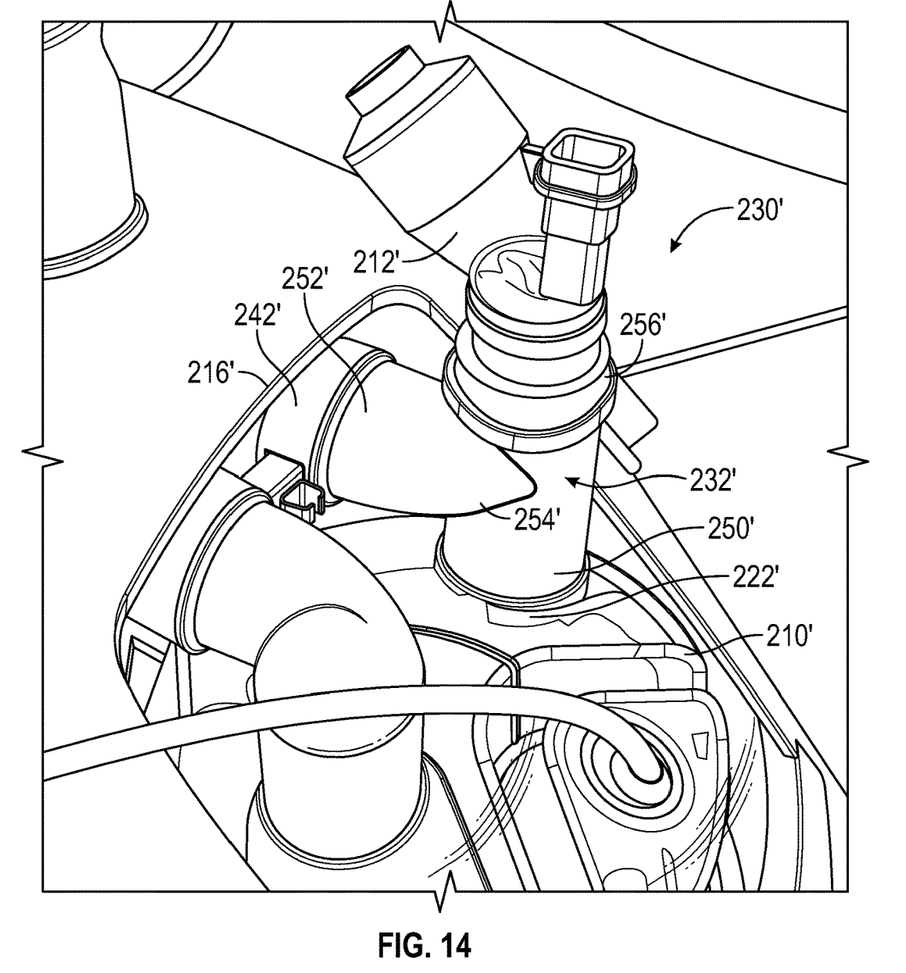
FIG. 14 is a view of another respiratory therapy system having a different mount.
Figure 15:
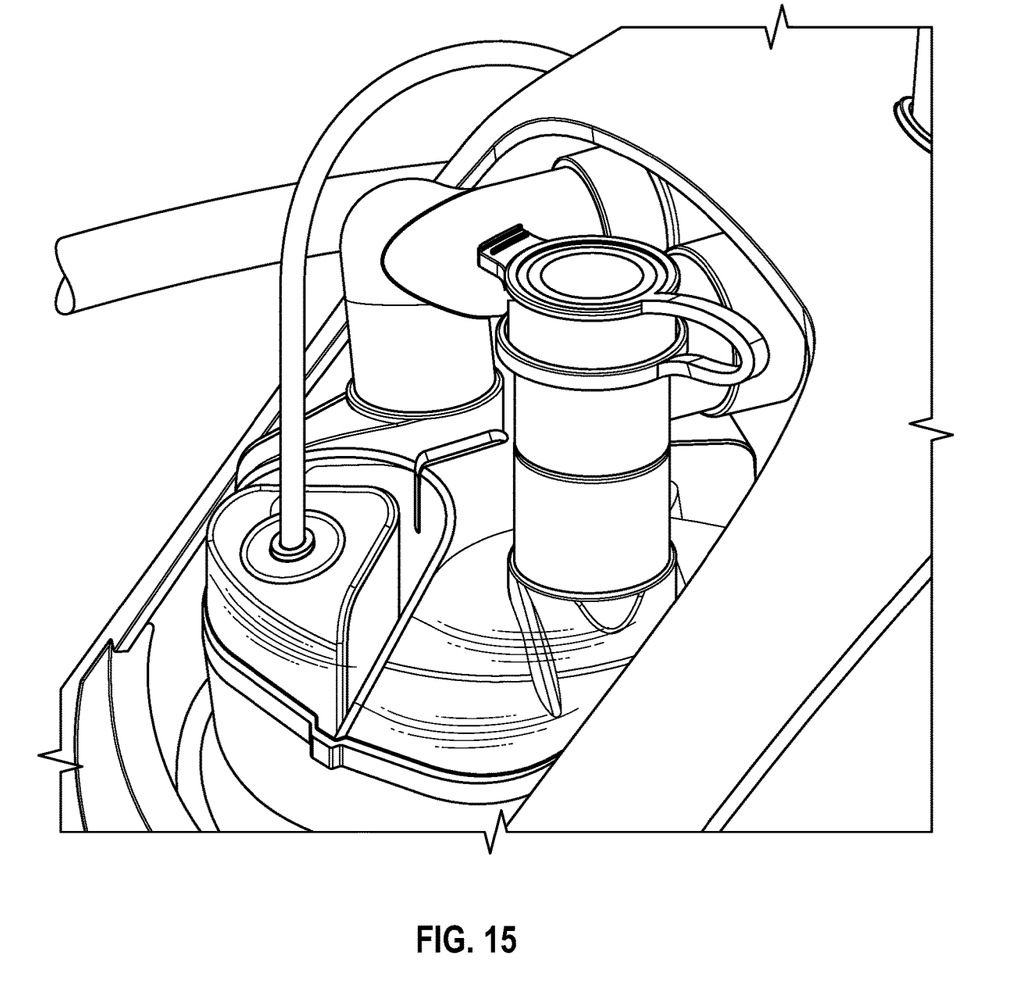
FIG. 15 is another view of system of FIG. 14 with the nebuliser removed.

With reference now to FIGS. 14 and 15, a second configuration of the mount 230' is illustrated. The second configuration of the mount 230' is configured the same as the first configuration of the mount 230 with the exception of the outflow duct 232'.

In the second configuration of the mount 230', the outflow duct 232' comprises a first portion 250' and a second portion 252' that are connected at a bend or elbow 254'. The first portion 250' extends vertically in the illustrated configuration. The illustrated second portion 252' extends horizontally. The second portion 252' intersects the first portion 250' at an intermediate location along the length of the first portion 250'. Other configurations are possible.

In the illustrated configuration, the first portion 250' can include an internal taper or the like. The first portion 250' seals or mates with an outer surface of the chamber outlet port 222'. The second portion can include the collar 242'. As described above, the collar 242' seals or mates with the post-chamber port 216'.

In the illustrated configuration, the first portion 250' comprises a second collar 256'. The second collar 256' is at an opposite end of the first portion 250' relative to the portion that connects to the chamber outlet port 222'. The second collar 256' can be sized and configured to mate or seal with the nebuliser 212'. In the illustrated configuration, the nebuliser 212' is received within the second collar 256'. More particularly, in the illustrated configuration, the inner surface of the second collar 256' includes a tapered surface that mates or seals with the outer surface of the nebuliser 212'. Other configurations are possible.

As illustrated in FIG. 14, the end of the first portion 250' proximate the chamber 210' and the second collar 256' are disposed at opposite ends of the first portion 250' of the outflow duct 232'. The first portion 250' of the outflow duct 232' can be a straight section of tubing or the like. In other words, in the illustrated configuration, the first end and the second collar 256' are aligned along a single axis that extends through the first portion 250' of the outflow duct 232'. In some configurations, a single plane that extends along the central axis of the first portion 250' of the outflow duct 232' bisects the first end and the second collar 256'. Other configurations are possible.

High Flow Therapy With Nebuliser and Smooth Bore Tubing

Figure 16:
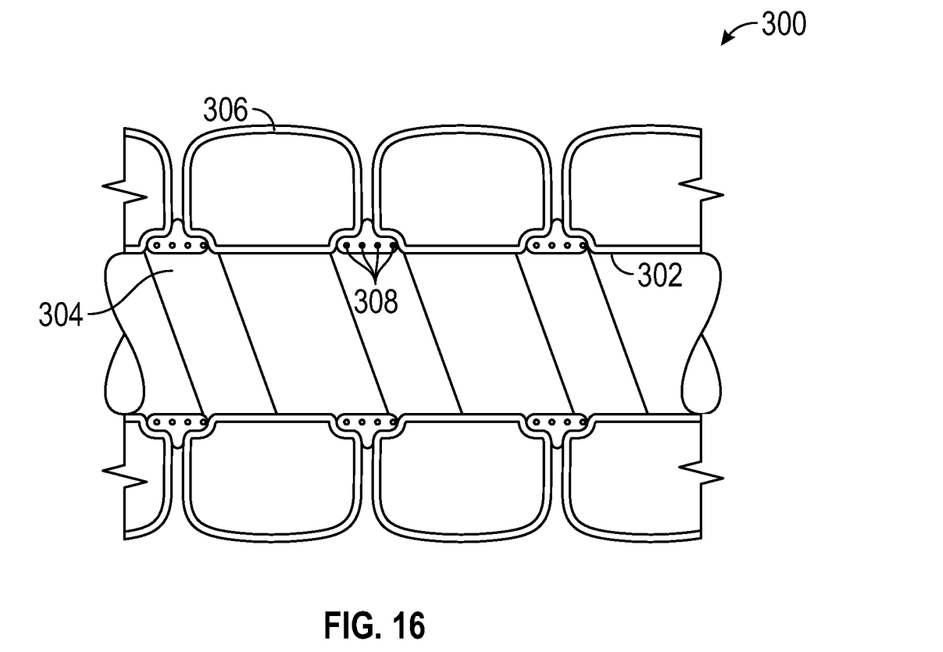
FIG. 16 is a sectioned view of a smooth bore conduit.
Figure 17:
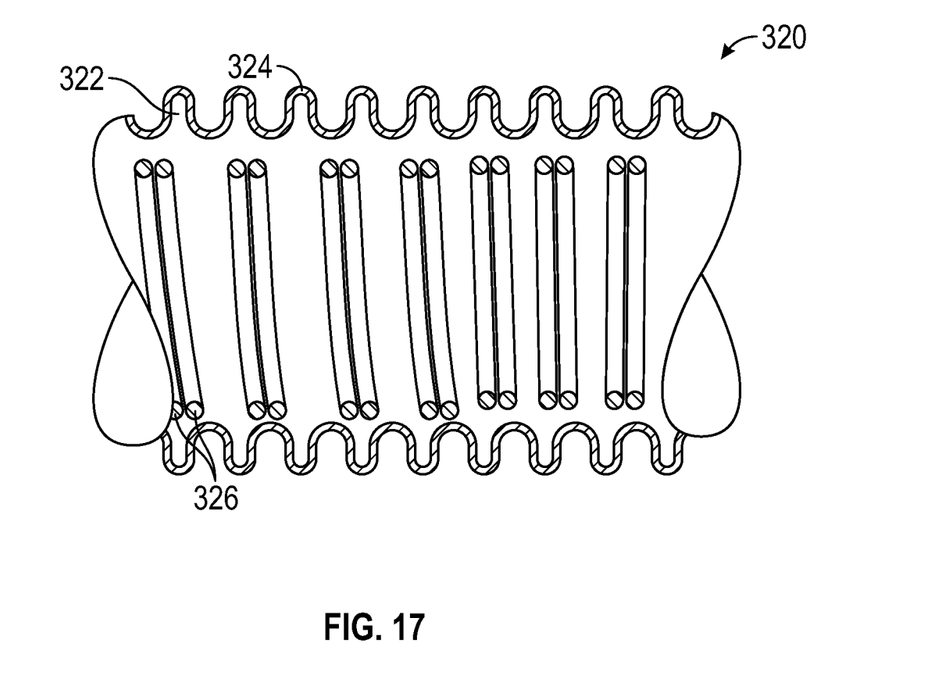
FIG. 17 is a sectioned view of a corrugated conduit.

With reference to FIGS. 16 and 17, two different types of tubing or conduit are represented in section. In FIG. 16, tubing or conduit 300 is illustrated featuring a smooth bore 302 or a non-corrugated bore. This type of tubing is best described and illustrated in in U.S. Patent Publication No. 2014/0202462A1 (also published as WO2012/164407A1) and WO2014/088430, for example, each of which is hereby incorporated by reference in its entirety. As described therein, the tubing is formed of a bead 304 and a small tube or bubble 306. In general, the peak to valley surface roughness of such tubing is on the order of 0.15-0.25 mm. In one configuration, the conduit or tubing has an internal bore diameter of 13-14 mm. The two components 304, 306 combine to define a conduit or tube with a lumen that has minimal surface deviations. In some configurations, the bead 304 contains wires 308. One or more of the wires can be used for heating the wall of the conduit without being positioned within the flow being conveyed by the conduit or tubing 300. In the illustrated configuration, the bead 304 contains four wires 308. In some configurations, the bead 304 may contain two wires 308. Other number of wires also can be used.

With reference to FIG. 17, the illustrated conduit or tubing 320 is corrugated tubing. In one configuration, the conduit or tubing 320 has an internal bore diameter of 20-21 mm. The corrugated tubing 320 includes deep furrows 322 along a wall 324 of the tubing 320. In many cases, the furrows 322 result in one or more helical interruption that extends along a length of the lumen defined by the wall 324. As such, the inner surface of the conduit or tubing is significantly rougher than the smooth bore tubing 300 illustrated in FIG. 17. In general, the corrugated conduit or tubing has peak to valley surface roughness on the order of 1.5-2.5 mm. In the illustrated configuration of FIG. 17, one or more heating wires 326 also can be coiled and positioned in direct contact with the gas flow through the lumen. When the wires are positioned within the gas flow path, the heater wire adds 2-3 mm of added "surface roughness" although this is merely an estimate of the effect of the heater wire being positioned within the gas flow path.

Surprisingly, use of the smooth bore heating tube 300, such as that illustrated in FIG. 16, for use in drug transportation from the nebuliser 212/212' described above, has resulted in significant increases in drug transportation efficiency compared to use of a more conventional heated breathing tube 320, such as that illustrated in FIG. 17. The efficiency improvement is believed to be due to a large reduction of the amount of nebulised drug being caught within the furrows 322 and the exposed heating wires 326 of the more conventional heated breathing tube 320. For example, it has been estimated that 300% more of the nebulised drug is captured by the surfaces than that which is retained within the smooth bore heated breathing tube 300, such as that shown in FIG. 16, for example but without limitation. It is believed there is a reduction in the deposition processes, such as impaction, due to less vorticity in the flow and less obstacles that present an effective roughness.

A test was conducted in which a nebuliser solution was injected into a gas stream using the configuration described above. The nebuliser solution was a mixture of sodium chloride and green food coloring. The sodium chloride was at a 7% concentration in a volume of 90 ml (available from BioMed Limited in Auckland, NZ). The weight NaCl per 90 ml bottle was 6.3 grams, which results in a weight NaCl/ml of 0.07 grams/ml. The dosage used was 3 ml, which resulted in a dose of NaCl of 0.21 grams. The green food coloring had a concentration of 2.10% in a volume of 50 ml. The weight of the color per 50 ml bottle was 1.05 grams. The weight of color/ml was 0.021 grams. The mixture was 90 ml of NaCl 7% with 9 ml added food coloring. As such, the fraction of NaCl solution was 0.8889 and the fraction of the food coloring was 0.1111. The total drug volume was 3 ml, which resulted in a volume of NaCl solution of 2.666667 ml and a volume of 0.333333 ml of food coloring. A 2.666667 ml nebuliser solution volume included 0.333333 ml of food coloring (10%), which resulted in a weight of 0.007 grams of coloring, 0.186667 grams of NaCl. Thus, the total dry weight of the drug was 0.193667 grams. The following represents the results obtained.

wall. A wetter wall may encourage or allow more drug to rain out (e.g., water droplets may create more surface area or more flow turbulence, or lower energy to cause the drug to condensate or rain out).

The respiratory therapy system can include a control system that receives inputs relative to auxiliary components. Those inputs can be used to control operations of the respiratory therapy system. In some configurations, the respiratory therapy system coordinates operation of auxiliary components. For example, in some configurations, an oxygen supply is provided. In some configurations, the nebuliser is provided. In such configurations, the respiratory therapy system can be controlled in accordance with operation of the auxiliary components. In such configurations, the respiratory therapy system can coordinate operation of the auxiliary components and the basic operations (e.g., heater plate temperature, flow rate, heated breathing tube temperature) of the respiratory therapy system. In some configurations, the oxygen concentration and the nebuliser activation (e.g., on/off state, frequency, output) can be controlled by a controller linked to the flow generator/humidifier.

In some configurations, when the flow rate exceeds an optimal flow rate, the transportation efficiency has been found to decrease. In other words, at some high flow rates above 30 lpm, the flow rate is somewhat inversely proportional to nebulisation efficiency (i.e., high flow rates result in more medication become trapped within the circuit instead of being delivered to the patient). Accordingly, the flow generator can be controlled based upon operation of the nebuliser. For example, the flow rate can be decreased when the nebuliser is installed. In some configurations, the flow rate can be decreased when the nebuliser is installed and operating (i.e., releasing medication). In some configurations, the flow rate can be decreased by a predetermined

| Experiment | Vol. Drug Delivered | Water Weight | Dilution Factor | Dilution Correction | Meas. Salinity | Overall "salt" content | Green Color 0 = most | % of Total | Ratio of current to 10 ml bubble |
|---|---|---|---|---|---|---|---|---|---|
| Corrugated HBT at 10 lpm | 3 ml | 134.646 | 5:50 | 11 | 109.8 | 162625.4 | 1 | 20.2% | 3.86 |
| Bubble HBT at 10 lpm | 3 ml | 95.123 | 5:25 | 6 | 73.8 | 42120.46 | 3 | 5.2% | 1.00 |
| Corrugated HBT at 30 lpm | 3 ml | 157.492 | 5:50 | 11 | 72.2 | 125080.1 | 2 | 15.5% | 2.97 |
| Bubble HBT at 30 lpm | 3 ml | 104.473 | 10:50 | 6 | 122.7 | 76913.02 | 3 | 9.5% | 1.83 |
| Drug in chamber after 4 experiments | 12 ml | 100.612 | — | 1 | 125 | 12576.5 | | 0.4% | |
| Simulate if all drug trapped in tube | 0.5 ml | 75 | 5:50 | 11 | 163 | 806850 | 0 | 100.0% | |

As shown above, during testing at a flow rate of 10 liters per minute of flow, about 20% of the drug was caught in the corrugated heated breathing tube while the heated smooth bore breathing tube retained only about 5% of the drug.

In some configurations, it is believed that heating the wall of the smooth bore heated breathing tube 300 may also act to reduce the retained drug. For example, it is posited that heating the wall can reduce condensation of water vapor on the wall or within the tube, which reduces the wetness of the amount (e.g., 15% or 20%) when the nebuliser is determined to be dispensing a substance. In some configurations, the flow rate can be lowered just before the release of substance by the nebuliser. In some configurations, the flow rate can be lowered just before the release of the substance by the nebuliser and maintained at the lowered rate for a predetermined period of time. In some configurations, the flow rate can be lowered just before the release of the substance by the nebuliser and the flow rate can be maintained at the lowered flow rate for a predetermined period of time sufficient to account for the time expected for the nebulised substance to reach the user or patient (i.e., the predetermined time can be a function of the flow rate).

In some configurations, the second conduit comprises the heated breathing tube, as discussed above. In some such configurations, the temperature of the heated breathing tube can be decreased when the nebuliser is installed. In some such configurations, the temperature of the heated breathing tube can be decreased when the nebuliser is installed and dispensing substance. In some such configurations, the temperature or duty cycle of the humidifier heater (e.g., heater plate) and/or the heated breathing tube can be decreased well before nebulised medication is added to the flow by the nebuliser. In some such configurations, the temperature or duty cycle of the humidifier heater and/or the heated breathing tube can be maintained lower for a predetermined period of time (or a period of time that is a function of the flow rate, for example). Such configurations can better account for thermal hysteresis in the system while protecting the nebulised substance from the excessive heat and/or possible thermal damage.

Method of Use

In some configurations, the respiratory therapy system 100 may be set up as follows. The steps can be conducted in any suitable order and, therefore, the following is a mere example of the order that can be used.

The integrated unit 103, 206, 206' can be positioned as desired.

The conduit can be connected to the unit 103, 206, 206'. The conduit can be a non-corrugated type of conduit. In some configurations, the conduit can be a smooth bore type of conduit. In some configurations, the conduit is a smooth bore type of conduit having a heated and insulating wall.

The mount 230, 230' is positioned on the chamber 210, 210'. The combined mount 230, 230' and chamber 210, 210' then are connected to the integrated unit 103, 206, 206'. The nebuliser 212 is connected to the mount 230, 230'.

Once assembled, the unit can be used with the nebuliser and conduit to provide any desired therapy capable of being performed with the combination of components. In some configurations, a nasal cannula is connected to the conduit and nasal high flow therapy is conducted while providing a drug via the nebuliser. Other configurations and methods also are possible.

Additional Configurations and Components of the System

In some configurations, the respiratory therapy system 100 may comprise a single user interface located on the first flow generator 101, the gas humidifier 112, the first conduit 110, the second conduit 122, the patient interface 124, or another component of the respiratory therapy system 100. In some configurations, the operation of components of the respiratory therapy system 100 may be actuated wirelessly using a user interface located on a remote computing device, which may be a tablet, a mobile phone, a personal digital assistant, or another computing device. In some configurations, the operation of the flow generator 101, of the gas humidifier 112, or of other components or aspects of the respiratory therapy system 100 may be controlled by a controller. The controller may comprise a microprocessor. The controller may be located in or on the flow generator 101, the gas humidifier 112, or other components of the respiratory therapy system 100 or on a remote computing device. In some configurations, multiple controllers may be used.

In some configurations, the respiratory therapy system 100 may comprise one or more sensors for detecting various characteristics of gases in the respiratory therapy system 100, including pressure, flow rate, temperature, absolute humidity, relative humidity, enthalpy, gas composition, oxygen concentration, and/or carbon dioxide concentration, one or more sensors for detecting various characteristics of the patient or of the health of the patient, including heart rate, respiratory rate, EEG signal, EKG/ECG signal, blood oxygen concentration, blood $CO_2$ concentration, and blood glucose, and/or one or more sensors for detecting various characteristics of gases or other objects outside the respiratory therapy system 100, including ambient temperature and/or ambient humidity. One or more of the sensors may be used to aid in the control of components (which may occur through use of the aforementioned controller) of the respiratory therapy system 100, including the gas humidifier 112, through the use of a closed or open loop control system. In some configurations, there may be no user interface or a minimal user interface for components of the respiratory therapy system 100. In some such configurations, the respiratory therapy system 100 may utilize a sensor to determine if the patient is attempting to use the respiratory therapy system 100 and automatically operate (e.g., the flow generator 101 may generate a gas flow, the gas humidifier 112 may humidify gases, the nebuliser 128 may nebulise a substance, etc.) according to one or more predetermined parameters if data obtained from the sensor indicates that the patient is attempting to use the respiratory therapy system 100.

It also should be understood that many configurations of the respiratory therapy system 100 may also be used for other applications not involving providing gases to an airway of a patient. For example, the respiratory therapy system 100 could instead be used for providing an insufflation gas in laparoscopic surgery. This may be enacted by replacing the patient interface 124 with a surgical cannula that may be inserted into an abdominal cavity that has been punctured with a trocar. If a nebuliser 128 is used, the nebuliser 128 may instead be configured to deliver the substance along with the insufflation gas to the abdominal cavity.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Recitation of ranges of values herein are merely intended to serve as a shorthand method of referring individually to each separate value falling within the range, unless otherwise indicated herein, and each separate value is incorporated into the disclosure as if it were individually recited herein. Additionally, each sub-range of values within ranges of values is incorporated into the disclosure as if it were individually recited herein.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A mount configured for use within a respiratory system, the mount being configured to join together a chamber, a flow-generating respiratory apparatus, and a third component, the mount comprising:
    a first duct, the first duct defining a three-way port comprising a first portion, a second portion, and a bend therebetween, the first portion of the first duct configured to connect to an outflow port of the chamber, and the first duct comprising an auxiliary port for interaction with a flow through the first duct, wherein the second portion of the first duct is configured to extend from the bend to the flow-generating respiratory apparatus in a first direction; and
    a second duct integrated with the first duct in a single structure, the second duct comprising a first portion, a second portion, and a bend therebetween, the first portion of the second duct configured to connect to an inflow port of the chamber, the second portion of the second duct is configured to extend from the bend of the second duct to the flow-generating respiratory apparatus in the first direction.

2. The mount of claim 1, wherein the auxiliary port is configured for connection to a nebulizer, a sensor, and/or a source of a trace gas.

3. The mount of claim 1, wherein the second portion of the second duct is configured to connect to a pre-chamber port of the flow-generating respiratory apparatus.

4. The mount of claim 1, wherein the auxiliary port receives a cap, the cap forming a removable sealed closure for the auxiliary port.

5. The mount of claim 1, wherein the auxiliary port is sized and configured to receive a nebulizer.

6. The mount of claim 1, wherein the second portion of the first duct and the second portion of the second duct extend along separate parallel axes.

7. A mount configured to couple a chamber to a flow-generating respiratory apparatus, the mount comprising:
    a duct configured to connect to one of an inlet port or an outlet port of the chamber, the duct comprising a 3-way port comprising:
        an auxiliary port;
        a flow inlet end configured to connect to the outlet port of the chamber;
        a flow outlet end configured to connect to a post-chamber port of the flow-generating respiratory apparatus with the auxiliary port being positioned in a flow path between the flow inlet end and the flow outlet end; and
        a bend between the flow inlet end and the flow outlet end,
    wherein a central axis extending through a lumen of the flow inlet end does not intersect a central axis extending through a lumen of the flow outlet end, and
    wherein the central axis extending through the lumen of the flow inlet end does not intersect a central axis extending through a lumen of the auxiliary port.

8. The mount of claim 7, wherein the mount comprises a second duct configured to connect to the inlet port of the chamber.

9. The mount of claim 7, wherein the auxiliary port receives a cap, the cap forming a removable sealed closure for the auxiliary port.

10. The mount of claim 7, wherein the auxiliary port is sized and configured to receive a nebulizer, a sensor, and/or a source of a trace gas.

11. A nebulizer mount configured to couple a chamber to a respiratory apparatus, the nebulizer mount comprising:
    an outflow duct, the outflow duct being configured to connect a post-chamber port of the respiratory apparatus, a chamber outlet port and a nebulizer port;
    an inflow duct, the inflow duct being configured to connect a pre-chamber port of the respiratory apparatus and a chamber inlet port; and
    a bridge joining the outflow duct and the inflow duct, the bridge being outside of a gases flow path passing through the outflow duct and the inflow duct, wherein the bridge is positioned entirely between the outflow duct and the inflow duct, wherein a first end of the bridge is connected to the outflow duct and a second end of the bridge is connected to the inflow duct;
    wherein the bridge comprises an external tube mount configured to receive a tube.

12. The nebulizer mount of claim 11 further comprising a cap configured to close the nebulizer port.

13. The nebulizer mount of claim 11, wherein a first end of the inflow duct is separated from a first end of the outflow duct by a first distance between flow passage centers and a second end of the inflow duct is separated from a second end of the outflow duct by a second distance between flow passage centers that is greater than the first distance.

14. The nebulizer mount of claim 11, wherein the outflow duct and the inflow duct are integrated into a single structure.

15. The nebulizer mount of claim 11 further comprising an outflow collar that defines at least a portion of a fitting configured to join the outflow duct to the post-chamber port and a taper being formed on an inner surface of the outflow collar.

16. The nebulizer mount of claim 11, wherein the outflow duct comprises a first portion and a second portion, the first portion being connected to the second portion by an elbow.

* * * * *